United States Patent [19]

Scharfenberg et al.

[11] Patent Number: 5,684,160
[45] Date of Patent: Nov. 4, 1997

[54] 3-AMINOPYRROLES, METHODS FOR THEIR SYNTHESIS AND FOR THEIR PHARMACEUTICAL USE

[75] Inventors: Peter Scharfenberg, Wuppertal; Jürgen Liebscher, Berlin; Alexander Knoll, Berlin; Aleksej Uschmajew, Berlin; Andreas Rolfs, Berlin; Dieter Lohman, Radebeul; Gottfried Faust; Eveline Morgenstern, both of Berlin, all of Germany

[73] Assignee: Arzneimettelwerk Dresden GmbH, Germany

[21] Appl. No.: 446,000

[22] Filed: May 19, 1995

Related U.S. Application Data

[62] Division of Ser. No. 614,459, Nov. 16, 1990, Pat. No. 5,502,051.

[51] Int. Cl.$^6$ .................................................. C07D 207/34
[52] U.S. Cl. ........................... 548/516; 548/518; 548/532; 546/208; 544/141
[58] Field of Search ............................... 548/516, 518, 548/532; 546/208; 544/141

[56] References Cited

U.S. PATENT DOCUMENTS 4,198,502  4/1980  Tarzia et al. ............................. 548/540

OTHER PUBLICATIONS

Knoll, et al.; Chimija Geterociklicheskih Soedinenijg (1985), No. 5, pp. 628–630 (Synthesis ester of substituted β-aminopyrrole-2-carboxylic acids from thioacrylic acids and glycine ethers.

Tarzia, et al.; Farmaco, Ed. Sci. (1984), 39(6), pp. 538–558; Synthesis and pharmacological evalution of a series of analgesic and antiinflammatory 4-aminopyrroles.

*Primary Examiner*—Robert Gerstl
*Attorney, Agent, or Firm*—Schweitzer Cornman Gross & Bondell LLP

[57] ABSTRACT

The invention is directed to 3-aminopyrroles of formula I, which are largely new, to methods for the preparation and to their use as medicinal agents and preparations, as well as to anti-convulsive or analgesic preparations containing these 3-aminopyrroles.

Disubstituted and monosubstituted amino groups are claimed as 3-amino substituents.

The invention pursues the objective of developing largely new 3-aminopyrroles, which have CNS activity, particularly ones which anti-convulsive or analgesic properties, as well as methods for their preparation and their use as medicinal preparations.

Pursuant to the invention, the synthesis is carried out by cyclizing open-chain precursors, such as aminoacrylic acid derivative, or by modifying pyrroles.

7 Claims, No Drawings

3-AMINOPYRROLES, METHODS FOR THEIR SYNTHESIS AND FOR THEIR PHARMACEUTICAL USE

This a divisional application of U.S. application for Letters Patent Ser. No. 07/614,459 filed on Nov. 16, 1990, now U.S. Pat. 5,502,051.

FIELD OF THE INVENTION

The present invention relates to 3-aminopyrroles, methods for their preparation, and for their pharmaceutical use. The 3-aminopyrroles of the present invention are useful for the treatment of central nervous systems (CNS) conditions, particularly for exerting an analgesic and anticonvulsive effect, with minimal or no side effects.

BACKGROUND OF THE INVENTION

3-Aminopyrroles have not previously been known to have an anticonvulsive effect. 3-Aminopyrroles, which in the 4-position have an aminocarbonyl group (German patent No. 2,605,419), or a carbonyl group (U.S. Pat. No. 4,198,502), have been described as having a CNS activity. This activity is actually referred to as sedating or analgesic, but neither published results were found nor were any confirmed by test results. These compounds are said to be prepared by modifying aminopyrrole derivatives, which in turn are obtained from α-aminonitriles and β-dicarbonyl compounds (German patents Nos. 2,605,419; 2,439,284; 2,462,967; 2,462,966: 2,462,963; British patent No. 1,492,663; and U.S. Pat. No. 4,198,502). Six esters of 3-morpholino-4-arylpyrrolecarboxylic acid with a very limited substitution pattern have been prepared by cyclizing 3-alkoxycarbonylmethylamino-2arylthioacrylic acid morpholidine (A. Knoll, J. Liebscher: Khim. Geterotsikl. Soedin 1985, 628). Nothing was found published about any pharmacological effect of such compounds. 3-Amino-4-arylpyrroles, the amino groups of which are, however, not substituted, were obtained by the reduction of the corresponding 3-nitropyrroles (J. M. Tedder, B. Webster: *J. Chem. Soc.* 1960, 3270).

3-Amino-2,4-diphenylpyrrole is described as being formed by the self-condensation of phenylacylamine (S. Gabriel: Ber. Dtsch. Chem. Ges. 41 (1908) 1127).

The known prior art does not describe any 3-amino-4-arylpyrroles, which are substituted at the amino group and have an anticonvulsive action. The substituent variability of the known compounds is very limited.

The compounds known as having anticonvulsive properties also have the disadvantage of unwanted side effects, such as neurotoxicity.

DESCRIPTION OF THE INVENTION

It is the object of the present invention to provide new 3-aminopyrroles with CNS activity, particularly those which have anticonvulsive or analgesic properties, methods or their preparation, and for their pharmaceutical use, and having low or negligible undesired side effects, such as neurotoxicity, in any event less than those of presently used anticonvulsive agents.

It was surprisingly found that 3-aminopyrroles of formula I have pharmaceutically valuable properties, including an anticonvulsive and analgesic effect.

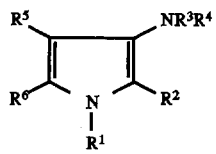

(I)

wherein $R^1$ is hydrogen, or a $C_1$–$C_{20}$, preferably $C_1$–$C_5$ alkyl, cycloalkyl, aralkyl, aryl or heteroaryl, acyl, alkoxycarbonyl residue, aminocarbonyl that is not substituted at the nitrogen, or an N-mono- or N,N-disubstituted aminocarbonyl, or aminothiocarbonyl residue; $R^2$ is hydrogen, or a formyl, acyl, carboxyl, oxycarbonyl, a $C_2$–$C_{20}$, preferably $C_2$–$C_5$ alkoxy-carbonyl, aryloxycarbonyl, aminocarbonyl that is not substituted at the nitrogen, N-mono- or N,N-disubstituted aminocarbonyl, aryl or heteroaryl, a cyano, or a nitro residue; $R^3$ is hydrogen, or A $C_1$–$C_{10}$, preferably $C_1$–$C_5$ alkyl, cycloalkyl, aralkyl, aryl or heteroaryl residue;

$R^4$ is the same as or different from $R^3$ and is a $C_1$–$C_{10}$ alkyl, cycloalkyl, or an aralkyl or aryl or heteroaryl residue, or $R^3$ and $R^4$ together are an alkyl bridge, which can also contain oxygen, sulfur or nitrogen as ring atom;

$R^5$ is an aryl, carboxyl, or heteroaryl residue, or $R^5$ and $R^6$ together are $C_1$–$C_{10}$ alkyl bridge, or $R^6$ is hydrogen, a $C_1$–$C_{10}$ alkyl or aryl residue or a halogen atom; and their pharmaceutically acceptable acid addition salts.

The compounds of formula I are new, excepting methyl 4-(p-chlorophenyl)-3-morpholinopyrrole-2-carboxylate; methyl and ethyl 3-morpholino-4-(p-tolyl)pyrrole-2-carboxylate; methyl and ethyl 3-morpholino-4-(p-tolyl)pyrrole-2-carboxylate; and the methyl ester of 4-(p-anisyl)-3-morpholinopyrrole-2-carboxylate. Therefore, if $R^1$ and $R^6$ are respectively hydrogen, and $NR^3R^1$ morpholino, then the new compounds of the present invention do not include those of formula I in which $R^2$ and $R^5$ are respectively methoxycarbonyl and phenyl, ethoxycarbonyl and phenyl, methoxycarbonyl and p-chlorophenyl, methoxycarbonyl and p-tolyl, ethoxycarbonyl and p-tolyl, and methoxycarbonyl and p-anisyl.

3-Aminopyrroles of formula I, include for example, 4-arylpyrrolecarboxylic acid esters, which have a morpholino, piperazino, 4-alkylpiperazino, piperidino, pyrrolidino, dimethylamino, diethylamino, diethanolamino or di-(β-alkoxyethyl)amino substitution in the 3 position. Further, included among the new compounds of formula I are: methyl ester of 3-dimethylamino-4-phenylpyrrole-2-carboxylic acid; benzyl ester of 3-morpholino-4-phenylpyrrole-2-carboxylic acid; 3-morpholino-4-phenylpyrrole-2-carboxylic acid; sodium salt of 3-morpholino-4-phenylpyrrole-2-carboxylic acid; anilide of 3-morpholino-4-phenylpyrrole-2-carboxylic acid; methyl ester of 4-phenyl-3-pyrrolidinopyrrole-2-carboxylic acid; ethyl ester of 4-phenyl-3-pyrrolidinopyrrole-2-carboxylic acid; methyl ester of 1-methyl-3-morpholino-4-phenylpyrrole-2-carboxylic acid; methyl ester of 1-benzyl-3-morpholino-4-phenylpyrrole-2-carboxylic acid; methyl ester of 1-ethoxycarbonylmethyl-3-morpholino-4-phenylpyrrole-2-carboxylic acid; methyl ester or 1-methyl-3-morpholino-4-(p-tolyl)pyrrole-2-carboxylic acid; ethyl ester of 3-piperidino-4-(p-tolyl)pyrrole-2-carboxylic acid; methyl ester of 3-morpholino-4-(p-tolyl)pyrrole-2-carboxylic acid; methyl ester of 4-(m-anisyl)-3-morpholinopyrrole-2-carboxylic acid; methyl ester of 4-(p-anisyl)-3-morpholinopyrrole-2-carboxylic acid; ethyl ester of 4-(p-anisyl)-3-morpholinopyrrole-2-carboxylic acid; methyl ester of 4-(p-fluorophenyl)-3-morpholinopyrrole-2-carboxylic acid; ethyl ester of 4-(p-chlorophenyl)-3- morpholinopyrrole-2-carboxylic acid; methyl ester of 4-(p-chlorophenyl)-1-methyl-3-morpholinopyrrole-2-carboxylic acid; ethyl ester of 4-(p-chlorophenyl)-1-methyl-3-morpholinopyrrole-2-carboxylic acid; methyl ester of 1-benzyl-4-(p-chlorophenyl)-3-morpholinopyrrole-2-carboxylic acid; methyl ester of 4-(p-chlorophenyl)-3-piperidinopyrrole-2-carboxylic acid; methyl ester of 4-(m-bromophenyl)-3-morpholinopyrrole-2-carboxylic acid; methyl ester of 4-(p-bromophenyl)-3-morpholinopyrrole-2-carboxylic acid; methyl ester of 4-(p-bromophenyl)-1-methyl-3-morpholinopyrrole-2-carboxylic acid; methyl ester of 4-(p-bronmphenyl)-1-ethyl-3-morpholinopyrrole-2-carboxylic acid; methyl ester of 3-morpholino-4-(p-phenylphenyl)pyrrole-2-carboxylic acid; methyl ester of 4-(3,4-dimethoxyphenyl)-3-morpholinopyrrole-2-carboxylic acid; ethyl ester of 3-anilino-4,5-pentamethylenepyrrole-2-carboxylic acid; and 2-acetyl-4-(p-chlorophenyl)-3-morpholinopyrrole.

The present invention also provides, methods for preparing 3-aminopyrroles of formula 1. Accordingly, the method of preparation involves reacting (a) an aminoacrylic acid derivative of formula II

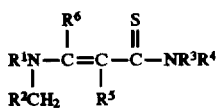
(II)

in which $R^1$, $R^2$, $R^3$, $R^4$, or respectively $R^3/R^4$, $R^5$ and $R^6$, or respectively $R^5/R^6$ have the same meaning as given above, or an aminoacrylic acid derivative of formula III

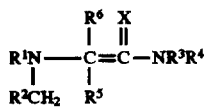
(III)

in which $R^1$, $R^2$, $R^3$, $R^4$ or respectively $R^3/R^4$, $R^5$ and $R^6$, or respectively $R^5/R^6$ have the same meaning as given above, and in which X is oxygen, or a substituted nitrogen atom, with (b), an oxidizing agent, or a dehydrating agent, or both a dehydrating agent and an oxidizing agent, when required then also with an alkylating agent, preferably in the presence of a base.

3-aminopyrroles of formula I can also be obtained by cyclizing (i) a trimethinium salt of formula IV

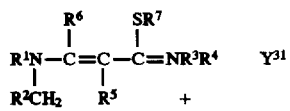
(IV)

wherein $R^1$, $R^2$, $R^3$, $R^4$ or respectively $R^3/R^4$, $R^5$ and $R^6$, or respectively $R^5/R^6$ have the same meaning as given above, and wherein $R^7$ is an alkyl, or aralkyl residue, and $Y^-$ is an acid group anion such as a halide, perchlorate, alkyl sulfate, sulfonate, sulfate, tetrafluoroborate, tetraaryl borate, or picrate ion, or (ii) the associated free base of a trimethinium salt of formula IV, or (iii) a trimethinium salt of formula V

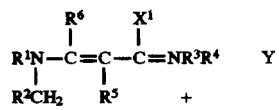
(V)

wherein $R^1$, $R^2$, $R^3$, $R^4$ or respectively $R^3/R^4$, $R^5$ and $R^6$, or respectively $R^5/R^6$, $Y^-$ have the same meaning as given above, and wherein $X^1$ is a leaving group, such as a halogen, alkoxy, or amino residue, and $Y^-$ is an acid ester anion such as a halide, perchlorate, alkyl sulfate, sulfonate, sulfate, tetrafluoroborate, tetraarylborate, or picrate ion, or (iii) the associated free base of a trimethinium salt of formula V, preferably in the presence of a base.

Furthermore, 3-aminopyrroles of formula I can be prepared by reacting (a) an (i) acrylamide derivative of formula VI

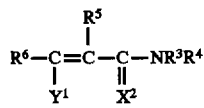
(VI)

wherein $R^3$, $R^4$, or respectively $R^3/R^4$, $R^5$ and $R^6$, or respectively $R^5/R^6$ have the same meaning as given above, and wherein $X^2$ is oxygen, sulfur, or a monosubstituted or disubstituted nitrogen atom, and $Y_1$ is a leaving group, such as an amino, alkylthio, alkoxy, hydroxy, mercapto, acyloxy, or a halogen residue, or (ii) an iminium salt of formula VIII

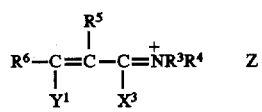
(VIII)

wherein $R^3$, $R^4$, or respectively $R^3/R^4$, $R^5$ and $R^6$, or respectively $R^5/R^6$ have the same meaning as given above, and wherein $X^3$ and $Y^1$ are the same or are different, and are a leaving group, such as an amino, alkylthio, alkoxy, hydroxy, mercapto, acyloxy, or halogen residue, and Z is an acid group anion such as a halide, perchlorate, alkyl sulfate, sulfonate, sulfate, tetrafluoroborate, tetraaryl borate, or picrate ion, with (b) an amine of formula VII

$R^2CH_2NHR^1$ (VII)

wherein $R^1$ and $R^2$ have the same meaning as given above, in the presence of (c) an oxidizing agent, and if required an alkylating agent, and preferably in the presence of a base.

3-Aminopyrroles of formula I, in which $R^2$, $R^3$, $R^4$, or respectively $R^3/R^4$, $R^5$ and $R^6$, or respectively $R^5/R^6$ have the same meaning as given above, and wherein $R^1$ is an alkyl, cycloalkyl, or an aralkyl residue, can also be prepared by reacting (a) a 3-aminopyrrole, of formula IX which is not substituted in the 1 position

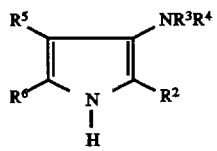
(IX)

wherein $R^2$, $R^3$, $R^4$, or respectively $R^3/R^4$, $R^5$ and $R^6$, or respectively $R^5/R^6$ have the same meaning as given above, with (b) an alkylating agent of formula X

$R^1-Y^2$ (X)

wherein $R^1$ has the same meaning as given above, and $Y^2$ is a leaving group, such as a halogen, sulfonyloxy, or diazo residue, and (c) a base.

3-Aminopyrroles of formula I, wherein $R^1$, $R^3$, $R^4$, or respectively $R^3/R^4$, $R^5$ and $R^6$, or respectively $R^5/R^6$ have the same meaning as given above, and wherein $R^7$ is $COZ^1$ wherein $Z^1$ is hydroxy, or metal-O, alkoxy, or an amino residue, can be prepared by the reaction of (a) a pyrrolecarboxylic acid derivative of formula XI

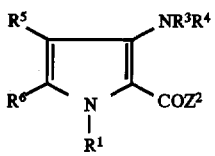

wherein $R^1$, $R^3$, $R^4$, or respectively $R^3/R^4$, $R^5$ and $R^6$, or respectively $R^5/R^6$ have the same meaning as given above, and wherein $Z^2$ is different from $Z^1$ and is a leaving group, such as hydroxy, alkoxy, aryloxy, acyloxy, alkylthio, or a halogen residue, with (b) a nucleophilic reagent of formula XII

wherein $Z^1$ has the same meaning as given above; or with a deprotonated form of a nucleophilic reagent of Formula XII, and optionally with an acid, or a base.

3-Aminopyrroles of formula I, in which $R^1$, $R^2$, $R^3$, $R^4$, or respectively $R^3/R^4$, $R^5$ and $R^6$, or respectively $R^5/R^6$ have the same meaning as given above, can also be prepared by the reaction of (a) an (i) enamine derivative of formula XIII

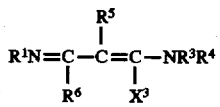

wherein $R^1$, $R^4$ or respectively $R^3/R^4$, $R^5$ and $R^6$, or respectively $R^5/R^6$ have the same meaning as given above, and in which $X^3$ is a leaving group, such as an alkoxy, alkyl-mercapto or substituted amino group or a halogen, or (ii) a salt of an enamine derivative of Formula XIII, such as a hydrohalide, a hydroperchlorate, a hydrosulfonate or a hydrotetrafluoroborate, with (b) an alkylating agent of formula XIV,

wherein $R^2$ has the same meaning as given above, and $Z^3$ is a leaving group, such as a halogen, sulfonate, alkyl sulfate, or a triflate (trifluoromethanesulfonic acid salt).

3-Aminopyrroles of formula I, in which $R^1$, $R^2$, $R^3$, $R^4$, or respectively $R^3/R^4$, $R^5$ and $R^6$, or respectively $R^5/R^6$ have the same meaning as given above, can also be prepared by reacting (a) an enamine of formula XV

wherein $R^1$, $R^2$, $R^5$ and $R^6$, or respectively $R^5/R^6$ have the same meaning as given above, with (b) an iminium salt of formula XVI

wherein $R^3$ and $R^4$, or respectively $R^3/R^4$ have the same meaning as given above, and $Y^3$ and $Y^4$ are the same or different leaving groups, such as chloro, amino, alkylmercapto or alkoxy residues, and $Y^-$ is an acid group anion, such as a halide, sulfonate, sulfate or a triflate, and optionally in the presence of (c) a base.

3-Aminopyrroles of formula I, in which $R^1$, $R^3$, $R^4$, or respectively $R^3/R^4$, $R^5$ and $R^6$, or respectively $R^5/R^6$ have the same meaning as given above, and $R^2$ is $R^7C=Z^4$, wherein $R^7$ is hydrogen, or an alkyl, aryl, or alkoxy residue, and $NHR^6$ wherein $R^6$ is alkyl, aryl, or heteroaryl residue, and $Z^4$ is an oxygen, sulfur or nitrogen atom, can be prepared by reacting (a) a 3-aminopyrrole of formula XVII, which is not substituted in the 2 position,

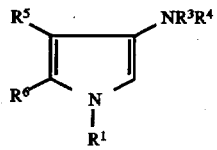

wherein $R^1$, $R^3$, $R^4$, or respectively $R^3/R^4$, $R^5$ and $R^6$, or respectively $R^5/R^6$ have the same meaning as given above, with (b) a carbonyl compound of formula XVIII

wherein $R^7$ and $Z^4$ have the same meaning as given above, and $Z^5$ is a leaving group such as halogen or acyloxy, or if in the compound of formula I wherein $R^2$ is $R^7C=Z^4$ wherein $R^7$ is a substituted amino group, $NHR^8$, also with (c) a heterocumulene of formula XIX

wherein $R^6$ and $Z^4$ have the same meaning as given above, and optionally in the presence of a Lewis acid, or a protonic acid.

Further, 3-aminopyrroles of formula I, wherein $R^1$, $R^2$, $R^3$, $R^4$, or respectively $R^3/R^4$, $R^5$ and $R^6$, or respectively $R^5/R^6$ have the same meaning as given above, can also be prepared by reacting (a) a 3-substituted pyrrole of formula XX

wherein $R^1$, $R^2$, $R^5$ and $R^6$, or respectively $R^5/R^6$ have the same meaning as given above, and $X^4$ is a leaving group, such as halogen, hydroxy, alkoxy, alkylthio, or the diazonium group, with (b) an amine of formula XXI

in which $R^3$, $R^4$, or respectively $R^3/R^4$ have the same meaning as given above.

Finally, 3-aminopyrroles of formula I, in which $R^1$, $R^3$, $R^4$, or respectively $R^3/R^4$, $R^5$ and $R^6$, or respectively $R^5/R^6$ have the same meaning as given above, and $R^5$ is $COOR^7$ wherein $R^7$ is an alkyl residue, can also be prepared by the reaction of a (a) 3-aminopyrrolecarboxylic acid of formula XXII

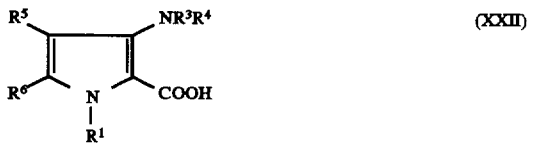

wherein $R^1$, $R^3$, $R^4$, or respectively $R^3/R^4$, $R^5$ and $R^6$, or respectively $R^5/R^6$ have the same meaning as given above, or of a salt of a 3-aminopyrrolecarboxylic acid of formula XXII, such as a sodium, potassium or ammonium salt, with (b) an alkylating agent of formula XXIII $$R^7X^5 \quad (XXIII)$$

wherein $R^7$ has the same meaning as given above, and $X^5$ is a leaving group, such as a halogen or a sulfonyl group, and (c) optionally in the presence of a base.

Suitably an amine, alkali or alkaline earth hydroxide or hydride, or an alkali carbonate, or metal amide can be used as the base.

The compounds of formula I have a surprising anticonvulsive analgesic utility for treating CNS conditions, particularly forms of epilepsy, non epileptic spasms, migraine, and other forms of pain than migraine. In tests with various convulsion models, the 3-aminopyrroles of formula I show a high anticonvulsive effect and are distinguished by a low toxicity and, above all by a protective index which is significantly higher than that of presently known conventional commercial anticonvulsive agents. The anticonvulsive effect is surprising, because such an effect has not previously been generally known in the case of 3-aminopyrroles.

The new, active substances of the present invention can also be included in a manner known per se into conventional dosage forms such as tablets, capsules, coated pills, granulates, or solutions, by using inert, non-toxic, pharmaceutically suitable carrier materials or solvents. Suitably from about 5 to about 20 mg/kg body weight of the 3-aminopyrrole constitutes an appropriate dose.

It is to be understood that by reference throughout the specification and the claims to any alkyl and aryl substituents in any of the formulae herein, substituted or unsubstituted moieties are also meant to be included. Furthermore, any reference to numbers of carbon atoms is made with respect to the numbers of carbon atoms in any unsubstituted moiety or substituted aryl nucleus, exclusive of any carbon atoms in any substitution among any subsidiary substituent moieties.

The present invention is further disclosed by the following illustrative examples. Examples 1–23 deal with the preparation of 3-aminopyrroles of formula I. The 3-aminopyrroles of these examples are also summarized in Table 1.

EXAMPLE 1

A solution of 10 mmoles of the aminoacrylic acid derivative of formula II and 1.9 g of dimethyl sulfate, or 2.2 g of methyl iodide in 20 ml of chloroform is heated under reflux for 15 minutes. After the solvent is drawn off, the residue is diluted with 10 ml of ethanol, or methanol and 1 g of triethylamine is added to the mixture, which is then heated for 5 minutes at boiling and, after cooling, is diluted with a little water. The resulting 3-aminopyrrole of formula I is filtered off with suction and is recrystallized.

EXAMPLE 2

A suspension of 10 mmoles of the aminoacrylic acid derivative of formula II in 10 ml of water is treated dropwise with 30 mmoles of 30% hydrogen peroxide with cooling, so that the temperature remains below 20° C. The reaction is allowed to go to completion during 30 minutes at room temperature, after which the temperature is lowered to 5° C. The solid product is filtered off with suction and treated with 10 ml acetonitrile and 2 ml triethylamine. The mixture is heated to boiling for 30 minutes and, after cooling, diluted with a little water. The resulting end product of formula I is filtered off with suction and is then recrystallized.

EXAMPLE 3

A solution of 10 mmoles of the aminoacrylic acid derivative of formula III wherein X is O is treated with 10 ml acetic anhydride and 2 ml ethyl diisopropylamine. The mixture is refluxed for 2 hours and then hydrolyzed with excess water. The resulting 3-aminopyrrole of formula I is filtered off with suction and is then recrystallized.

EXAMPLE 4

The trimethinium salt (10 mmoles) of formula IV, wherein $R^7$ is methyl, and $Y^-$ is $I^-$, is mixed with 10 ml ethanol and a solution of 0.4 g of sodium in 5 ml ethanol, and is heated for 30 minutes on a boiling water bath. After it has cooled down, the reaction mixture is neutralized under cooling with glacial acetic acid and diluted with a little water. The resulting end product of formula I is filtered off with suction and is then recrystallized.

EXAMPLE 5

A solution of 10 mmoles of a trimethinium salt of formula V wherein $X^1$ is Cl, and Y is chloride in 11 ml of ethanol is mixed with 1 ml of 1,8-diazabicyclo[5.4.0]-undecene and heated for 15 minutes at 50° C. The resulting 3-aminopyrrole of formula I, which precipitates on cooling, is filtered off with suction, washed with a little water, and is then recrystallized.

EXAMPLE 6

A solution of 10 mmoles of the trimethinium salt of formula V wherein $X^1$ is O-ethyl, and $Y^-$ is $BF_4^-$ in 10 ml acetonitrile, is mixed with 1 g of potassium carbonate and heated under reflux for 20 minutes. After it has cooled down, the reaction mixture is neutralized under cooling with hydrochloric acid. The product is filtered off with suction and is then recrystallized.

EXAMPLE 7

An acrylamide derivative (10 mmoles) of formula VI, wherein $X^2$ is S, and $Y^1$ is dimethylamino, is treated in the form of its hyperchlorate with 15 ml methanol, 10 mmoles of an amine of formula VII, and 3 g of triethylamine. The mixture is heated to boiling for 5 minutes, cooled down and diluted with a little ice water. The precipitate is filtered off with suction, dried, mixed with 10 ml of ethanol and 2 g of methyl p-toluenesulfonate and heated under reflux for 10 minutes. After the addition of 2 ml of triethylamine, heating under reflux is continued for a further 10 minutes. If the end product does not precipitate on cooling, then the reaction mixture is diluted with a little cold water. The product is filtered off with suction and recrystallized.

EXAMPLE 8

The procedure of Example 7 is followed, except that an acrylamide derivative of formula VI wherein $X^1$ is S, and $Y^1$ is OH, is used and the amine of formula VII is used as hydrochloride.

EXAMPLE 9

A mixture of 10 mmoles of an imininium salt of formula VIII wherein $X^3$ is methylmercapto, $Y^1$ is dimethylamino, and $Z^-$ is $I^-$, with 15 ml ethanol is mixed with 10 mmoles of an amine of formula VII, and heated briefly to boiling. After the addition of 2 ml of triethylamine, the mixture is heated for 30 minutes under reflux and then allowed to cool down. If necessary, a little water is added and the end product of formula I is filtered off with suction and is then recrystallized.

EXAMPLE 10

The procedure of Example 9 is followed, except that an iminium salt of formula VIII, wherein $Y^1$ is morpholino, and $X^3$ is chloro, and $Z^-$ is $Cl^-$, is used.

EXAMPLE 11

A solution of 5 mmoles of 3-aminopyrroles of formula IX in 40 ml of methylene chloride is mixed with 7.5 mmoles of the alkylating agent of formula X, wherein with $Y^2$ is Br or I, and with 0.05 g of benzyltriethylammonium bromide. After the addition of a solution of 0.05 g of benzyltriethylammonium bromide in 15 ml 50% sodium hydroxide solution, the mixture is stirred vigorously for 5 hours at room temperature and then neutralized with dilute hydrochloric acid. The organic phase is separated and the aqueous phase is extracted twice with methylene chloride. The combined organic extracts are washed with water and potassium carbonate solution. After drying over sodium sulfate, the solvent is evaporated. The resulting end product of formula I crystallizes upon the addition of a little water or cyclohexane.

EXAMPLE 12

The 3-aminopyrrole (10 mmoles) of formula IX is dissolved in 50 ml of tetrahydrofuran. The solution is cooled to 0° C. and 11 mmoles sodium hydride are added in portions with stirring. After that, 11 mmoles of alkylating agent of formula X wherein $Y^2$ is Cl, are also added. The mixture is allowed to stand for 1 hour at room temperature and subsequently refluxed for 1.5 hours. It is then allowed to cool down and filtered and the filtrate is concentrated. Upon the addition of a little ethanol or cyclohexane, the resulting end product of formula I crystallizes from the residue. It is filtered off with suction and is then recrystallized.

EXAMPLE 13

A mixture of 3 mmoles of pyrrolecarboxytic acid derivative of formula XI, wherein $Z^2$ is O-ethyl, 20 ml ethanol, and 8 ml 2N sodium hydroxide solution (corresponds to the deprotonated form of the nucleophilic reagent of formula XII wherein $Z^1$ is OH) is allowed to stand at room temperature for 2 hours and subsequently heated on boiling water bath for one hour. Upon cooling, the end product of formula I, wherein $R^2$ is COONa, crystallizes out. This is filtered off with suction. It can be converted to the corresponding free acid of formula I with $R^2$ is COONa by the addition of hydrochloric acid to the aqueous ethanolic solution.

EXAMPLE 14

A solution of 20 mmoles of pyrrolecarboxylic acid derivative of formula XI wherein $Z^2$ is methoxy, in 50 ml of a nucleophilic reagent of formula XII wherein $Z^1$ is ethoxy, is mixed with a solution of 0.23 g of sodium in 7 ml of ethanol and heated for 2 hours, during which time the solvent is gradually distilled off. When the distillation residue reaches a volume of about 6 mL, the distillation is discontinued and the residue is allowed to cool down. The precipitate is filtered off with suction, washed with a little cold ethanol, and is then recrystallized.

EXAMPLE 15

A solution of 10 mmoles of pyrrolecarboxylic acid derivative of formula XI wherein $Z^2$ is chloro, in 8 ml of acetonitrile is mixed with 10 mmoles of the nucleophilic reagent of formula XII, wherein $Z^1$ is phenyl-NH and 1 ml of triethylamine. After the exothermic reaction has subsided, the mixture is heated briefly to boiling. The resulting end product of formula I, which crystallizes out on cooling, is filtered off with suction, and is then recrystallized.

EXAMPLE 16

To a mixture of 2.8 g of potassium carbonate and 20 ml of dimethylformamide, 10 mmoles of the enamine derivative of formula XIII wherein $X^3$ is methylmercapto, and 12 mmoles of alkylating agent of formula XIV wherein $Z^3$ is Cl are added. Stirring at 100° C. is continued for 3 hours. After the addition of 2 ml of triethylamine, stirring is continued for 2 hours at 85° C. The reaction mixture is cooled down and then poured onto ice water. The end product is filtered off with suction, and is then recrystallized.

EXAMPLE 17

A solution of 10 mmoles of enamine of formula XV in 10 ml of acetonitrile is mixed with 10 mmoles of the iminium salt of formula XVI wherein both $Y^3$ and $Y^4$ are Cl, and $Y^-$ is $Cl^-$. After heating for 30 minutes on boiling water bath, 3 ml triethylamine are added and the mixture is refluxed for 30 minutes, then cooled down and poured onto ice. The end product of formula I is filtered off with suction, and is then recrystallized.

EXAMPLE 18

3-Aminopyrrole (10 mmoles) of formula XVII is dissolved in 10 ml of acetonitrile, mixed with 20 mmoles of carbonyl compound of formula XVIII wherein $Z^4$ is O and $Z^5$ is a chloro residue. The mixture is heated under reflux for 20 minutes, then cooled down and poured onto ice. The end product of formula I wherein $R^2$ is $COR^7$, is filtered off with suction, and is then recrystallized.

EXAMPLE 19

The method of Example 18 is employed, except that a carbonyl compound of formula XVII wherein $Z^4$ is O, and $Z^5$ is $OCOCH_3$, is used.

EXAMPLE 20

Pyrrole (10 mmoles) of formula XVII is dissolved in 10 ml of benzene and 10 mmoles of a heterocumulene of formula XIX wherein $Z^4$ is O, are added. After heating for 40 minutes under reflux, the solvent is distilled off and the residue is then recrystallized.

EXAMPLE 21

A 3-substituted pyrrole (10 mmoles) of formula XX wherein $X^4$ is methylthio, is dissolved in 10 ml of methanol or ethanol and is mixed with 10 mmoles of the amine of formula XXI. After heating under reflux for 30 minutes, a portion of the solvent is evaporated. The end product of formula I is filtered off with suction and is then recrystallized.

EXAMPLE 22

The method of Example 21 is repeated, except a 3-substituted pyrrole of formula XX is employed, wherein $X^4$ is a chloride residue.

EXAMPLE 23

The sodium salt (10 mmoles) of a 3-aminopyrrolecarboxylic acid of formula XXII is mixed with 10 ml acetonitrile, 10 mmoles alkylating agent of formula XXIII wherein $X^5$ is a bromo residue, and further with 1 mmole methyltrioctylammonium chloride, and 10 ml of water. The mixture is refluxed for 4 hours and then allowed to cool down, whereupon the organic phase is removed. The aqueous phase is extracted with ether, and the combined organic phases are dried and concentrated. The remaining end product is filtered off with suction, and is then recrystallized.

TABLE 1

3-aminopyrroles of formula I prepared by the various Examples

| Example | $R^1$ | $R^2$ | $R^3$ | $R^4$ | $R^5$ | $R^6$ | Melting Point | Yield % |
|---|---|---|---|---|---|---|---|---|
| 1 | H | $CO_2CH_3$ | $CH_3$ | $CH_3$ | $C_6H_5$ | H | 136–137 (methanol) | 73 |
| 10 | | | | | | | | 76 |
| 4 | H | $CO_2CH_3$ | $(CH_2)_2$ | $O(CH_2)_2$ | $C_6H_5$ | H | 179–181 (methanol) | 79 |
| 5 | H | $CO_2C_2H_5$ | $(CH_2)_2$ | $O(CH_2)_2$ | $C_6H_5$ | H | 171–172 (ethanol) | 88 |
| 9 | | | | | | | | 86 |
| 1 | H | $CO_2CH_2C_6H_5$ | $(CH_2)_2$ | $O(CH_2)_2$ | $C_6H_5$ | H | 165–167 (ethanol) | 97 |
| 22 | | | | | | | | 92 |
| 23 | | | | | | | | 86 |
| 13 | H | COOH | $(CH_2)_2$ | $O(CH_2)_2$ | $C_6H_5$ | H | 130–138 (dec.) (n-propanol) | 51 |
| 13 | H | $COON_a$ | $(CH_2)_2$ | $O(CH_2)_2$ | $C_6H_5$ | H | 188–200 (dec.) (water) | 82 |
| 1 | H | $CONHC_6H_5$ | $(CH_2)_2$ | $O(CH_2)_2$ | $C_6H_5$ | H | 269–270 (acetonitrile) | 36 |
| 15 | | | | | | | | 87 |
| 20 | | | | | | | | 74 |
| 1 | H | $CO_2CH_3$ | $(CH_2)_4$ | | $C_6H_5$ | H | oil | 71 |
| 1 | H | $CO_2CH_3$ | $(CH_2)_4$ | | $C_6H_5$ | H | oil* | 76 |
| 12 | $CH_3$ | $CO_2C_2H_5$ | $(CH_2)_2$ | $O(CH_2)_2$ | $C_6H_5$ | H | 86–88 (methanol) | 89 |
| 12 | $CH_2C_6H_5$ | $CO_6CH_3$ | $(CH_2)_2$ | $O(CH_2)_2$ | $C_6H_5$ | H | 112–114 (methanol) | 66 |
| | | | | | | | | 60 |
| 12 | $CH_2CO_2C_2H_5$ | $CO_2CH_3$ | $(CH_2)_2$ | $O(CH_2)_2$ | $CH_6H_5$ | H | 97–98 (methanol) | 67 |
| 3 | H | $CO_2CH_3$ | $(CH_2)_2$ | $O(CH_2)_2$ | $4-CH_3C_6H_4$ | H | 149–150 (methanol) | 36 |
| 21 | | | | | | | | 72 |
| 2 | H | $CO_2C_2H_5$ | $(CH_2)_2$ | $O(CH_2)_2$ | $4-CH_3C_6H_3$ | H | 173–175 (ethanol) | 32 |
| 20 | | | | | | | | 67 |
| 11 | $CH_3$ | $CO_2CH_3$ | $(CH_2)_2$ | $O(CH_2)_2$ | $4-CH_3C_6H_4$ | H | 109–111 (methanol) | 90 |
| 1 | H | $CO_2C_2H_5$ | $(CH_2)_5$ | | $4-CH_3C_6H_4$ | H | 118–120 naphtha | 45 |
| 1 | H | $CO_2CH_3$ | $(CH_2)_2$ | $O(CH_2)_2$ | $4-CH_3CH_2C_6H_4$ | H | 158.5 (methanol) | 71 |
| 1 | H | $CO_2CH_3$ | $(CH_2)_2$ | $O(CH_2)_2$ | $3-CH_3OC_6H_4$ | H | 159–160 (methanol) | 55 |
| 6 | H | $CO_2CH_3$ | $(CH_2)_2$ | $O(CH_2)_2$ | $4-CH_3OC_6H_4$ | H | 158–159 (methanol) | 54 |
| 1 | H | $CO_2C_2H_5$ | $(CH_2)_2$ | $O(CH_2)_2$ | $4-CH_3OC_6H_4$ | H | 167–168 (ethanol) | 51 |
| 1 | H · | $CO_2CH_3$ | $(CH_2)_2$ | $O(CH_2)_2$ | $4-FC_6H_4$ | H | 181–182 (methanol) | 56 |
| 18 | | | | | | | | 48 |
| 7 | H | $CO_2CH_3$ | $(CH_2)_2$ | $O(CH_2)_2$ | $4-ClC_6H_4$ | H | 192–193 (methanol) | 44 |
| 8 | | | | | | | | 48 |
| 1 | H | $CO_2C_2H_5$ | $(CH_2)_2$ | $O(CH_2)_2$ | $4-ClC_6H_4$ | H | 195–197 (ethanol) | 66 |
| 14 | | | | | | | | 89 |
| 19 | H | $COCH_3$ | $(CH_2)_2$ | $O(CH_2)_2$ | $4-ClC_6H_4$ | H | 172–173 (methanol) | 68 |
| 11 | $CH_3$ | $CO_2CH_3$ | $(CH_2)_2$ | $O(CH_2)_2$ | $4-ClC_6H_4$ | H | 116–118 (methanol) | 89 |
| 16 | | | | | | | | 17 |
| 11 | $CH_3$ | $CO_2C_2H_5$ | $(CH_2)_2$ | $O(CH_2)_2$ | $4-ClC_6H_4$ | H | 125–126 (ethanol) | 70 |
| 11 | $CH_2C_6H_5$ | $CO_2CH_3$ | $(CH_2)_2$ | $O(CH_2)_2$ | $4-ClC_6H_4$ | H | 155–156 (methanol) | 85 |
| 1 | H | $CO_2CH_3$ | $(CH_2)_5$ | | $4-ClC_6H_4$ | H | 122–123.5 (acetonitrile) | 74 |
| 1 | H | $CO_2CH_3$ | $(CH_2)_2$ | $O(CH_2)_2$ | $3-BrC_6H_4$ | H | 168–169 (methanol) | 61 |
| | | | | | | | | 48 |
| 1 | H | $CO_2CH_3$ | $(CH_2)_2$ | $O(CH_2)_2$ | $4-BrC_6H_4$ | H | 176–177 (methanol) | 59 |
| 11 | $CH_3$ | $CO_2CH_3$ | $(CH_2)_2$ | $O(CH_2)_2$ | $4-BrC_6H_4$ | H | 113–120 (methanol) | 70 |
| 11 | $CH_2CH_3$ | $CO_2CH_3$ | $(CH_2)_2$ | $O(CH_2)_2$ | $4-BrC_6H_4$ | H | 115–117 (methanol) | 66 |
| 1 | $CH_2CH_3$ | $CO_2CH_3$ | $(CH_2)_2$ | $O(CH_2)_2$ | $4-C_6H_5C_6H_4$ | H | 181–183 | 26 |

TABLE 1-continued 3-aminopyrroles of formula I prepared by the various Examples

| Example | $R^1$ | $R^2$ | $R^3$ | $R^4$ | $R^5$ | $R^6$ | Melting Point | Yield % |
|---|---|---|---|---|---|---|---|---|
| 1 | H | $CO_2CH_3$ | $(CH_2)_2$ | $O(CH_2)_2$ | 3,4-$(CH_3O)_2$ $C_6H_3$ | H | (methanol) 182–183 (acetonitrile) | 73 |
| 1 | H | $CO_2C_2H_5$ | H | $C_6H_5$ | $(CH_2)_4$ | | 192–194 (ethanol) | 81 |

*$^1$H-HMR($CDCl_3$) (ppm) (Multipl., number of H assignment; 1.34(t, 3H, $CH_3$); 1.83(m, 4H, $CCH_2CH_2C$); 3.21(t, 4H, $NCH_2$); 4.31(q, 2H, $OCH_2$); 7.24–7.57(m, 5H, $C_6H_5$); 9.30(br, 1H, NH); 6.82(d, 1H, CH).

The pharmacological utility of 3-aminopyrroles was established as described below.

Determination of the protection against the maximum electric convulsion (MEC)

An extension spasm of the rear extremities is initiated in mice weighing 18–22 gm, by electrical stimulation of the front paws with a TUR stimulating current instrument, model RS 12 manufactured by Tranformatoren -und R öntgenwerk "Hermann Mathern" of Dresden, Germany, (pulse frequency of 35 Hz, pulse width of 20 ms, duty factor of pulses 1:1, group duration of between 400 and 600 ms, current strength of square pulses 50 mA). Effective anticonvulsive agents are designed to protect the animals against the maximum electric convulsion. The test is described in greater detail in:

Toman, J. E. P., E. A. Swingyard, L. S. Goodman, Properties of Maximal Seizures and Their Alteration by Anticonvulsant Drugs and Other Agents, *J. Neurophysiol.* 9 (1946) 231–240.

Woodbory, D. M., J. K. Penry, C. E. Pippenger (EDS.,), *Antiepileptic Drugs*, 2.ED., pp 11–126, Raven Press, New York (1982).

Goodmann, L. S., M. S. Grewal, W. C. Brown, E. A. Swingyard, Comparison of Maximal Seizures Evoked by Pentylentetrazol (Metrazol) and Electroshock in Mice, and Their Modification by Anticonvulsants. *J. Pharmacol. Exp. Ther.* 108 (1953) 168–176.

Results:

Compounds of Examples 7, 8: after intraperitoneal administration: $E_{D50}$ is $3.9 \times 10^{-9}$ moles/kg after oral administration: $E_{D50}$ is $4.5 \times 10^{-9}$ moles/kg.

Compound of Example 1: after i.p administration $5 \times 10^{-4}$ moles/kg; 70%

Comparison values: "Carbamazepine": after intraperitoneal administration $L_{D50}$ is $4.3 \times 10^{-5}$ moles/kg.

Determination of the effect in the case of pentetrazoline-induced convulsion

Upon intravenous injection into the tail vein of mice weighing 18 to 22 g, an extension spasm of the rear extremities occurs immediately. Effective suppression of the development of this spasm was used as a criterion for determining the anticonvulsive effect of the substances tested. The test is described n greater detail in:

Marshall, R. G. and O. K. Valance, Anticonvulsant Activity, Derivatives of Succinimide, Glutarimide, Thiazolidinedione and Methanol, and some Miscellaneous Compounds. *J. Pharmacol.* (London) 6 (1954) 740–746.

Results:

Compounds of Examples 7, 8: after intraperitoneal administration: $E_{D50}$ is $4.5 \times 10^{-5}$ moles/kg, after oral administration: $E_{D50}$ is $1.5 \times 10^{-4}$ moles/kg.

Determination of the Convulsion Threshold

Through infusion of 100 mg/kg of pentetrazole at a rate of 36 ml/hour by way of the tail vein, clonic convulsions (myoclonic convulsions) are the first to occur in mice weighing 18 to 22 g. The prolonged infusion was carried out with a device sold under the name Lineomat, by MLW Injekta Klingenthal, from Chemnitz, Germany. The prolongation of the duration of the infusion (in seconds) until the occurrence of the convulsions, relative to the control animals, is regarded as the increase in the pentetrazole convulsion threshold and thus as the anticonvulsive effect of the substances tested. The test is described in the literature in greater detail in:

Hint, M. C. and Ricther, A. W., A Simple Intravenous Infusion Technique for Mice. Method and Some Applications, *Acta Pharmacol. Toxicol.* 14 (1958) 153–157.

Richter, A. W. Estimation of the I.V. Mean Lethal Dose for Mice by a Constant Infusion Titration, *Acta Pharmacol, Toxicol.* 15 (1958) 37–42.

Results:

Compound of Example 12: intraperitoneally at $5 \times 10^{-4}$ moles/kg: 20.4% increase in convulsion threshold.

Compound of Example 12: intraperitoneally at $5 \times 10^{-4}$ moles/kg: 19.4% increase.

Determination of the Orienting Lethal Dose

Mice, weighing 18 to 22 g, are administered the substances to be tested in dosages of $5 \times 10^{-4}$, $10^{-3}$, and $5 \times 10^{-3}$ moles/kg of body weight. The lethality of the animals is determined 24 hours after the administration. The test is described in the literature in greater detail in:

Irwin, S., Comprehensive Observational Assessment: A Systematic Quantitative Procedure for Assessing the Behavior of the Mouse, *Psychopharmacologia* 13 (1968) 222–237).

Campbell, D. E. S. and Richter, W., An Observational Method Estimating Toxicity and Drug Actions in Mice Applied to 68 Reference Drugs, *Acta Pharmacol. et Toxicol.* 25 (1967) 345–363.

Results:

Compound of Example 13: oLD greater than $5 \times 10^{-3}$ moles/kg.

Compound of Examples 7, 8: oLD greater than 5×10–3 moles/kg.

Determination of the analgesic effect with the hot plate test

Thirty minutes after the administration of the test substances, mice, weighing 18 to 22 g, were placed on a hot plate heated to 56° C. The reaction time to this thermal pain stimulation is determined. A prolongation of the refection time of animals treated with the test substance, relative to control animals, is rated as the analgesic effect. The test is described in the literature in greater detail in:

Janssen, P. A. J. and A. Jagenau, *J. Pharm. Pharmacol.* 9 (1957) 381, cit. in: R. A. Turner: Screening Method in Pharmacology, PP. 104–105, Academic Press, New York and London 1965.

Results:

Compound of Example 4: orally at $10^{-3}$ moles/kg: 90% inhibition (30 min. p.a.).

Comparison value: analgin (dipyrone): 55% inhibition.

Determination of the analgesic effect with the acetic acid writhing test

Abdominal wall cramps (writhings) were initiated in mice weighing 18 to 22 g by the intraperitoneal administration of 0.6% acetic acid. The reduction in the number of writhing reactions in treated animals, relative to those in the control group, is a measure of the strength of action of a substance. Aside from compounds with analgesic activity, various compounds with CNS activity also reduce the writhings. The test is described in greater detail in:

Koster, R., M. Anderson, E. J. De Beer, Acentic Acid For Analgesic Screening, *Fedn. Proc.* 18 (1959) 412.

Results:

Compound of Example 4: $10^{-3}$ moles/kg orally, 71.3% inhibition.

Compound of Example 13: $10^{-3}$ moles/kg orally, 84.2% inhibition $10^{-4}$ moles/kg orally, 50.2% inhibition.

Comparison: analgin: $10^{-4}$ moles/kg orally, 50% inhibition.

Determination of the neurotoxicity with the rotating rod model

After administration of the substance, trained mice, weighing 18 to 22 g, are placed on a rotating rod (5 revolutions per minute). Prematurely falling off the rotating rod is taken as a measure of the substance effect. The protective index is given by the ratio $TD_{50}/ED_{50}$ MEC (maximum electric convulsion). The test is described in greater detail in:

Dunham, N. W. and Miya, T. S., A Note on a Simple Apparatus for Detecting Neurological Deficits in Rats and Mice, *J. Am. Pharm. Assoc.* 46 (1957) 208–209. Results:

Compound of Examples 7, 8: $TD_{50}$ is $1.4 \times 10^{31\ 3}$ moles/kg, protective index is 36.

Comparison: carbamazepine: $TD_{50}$ $2.2 \times 10^{-4}$ moles/kg, protective index is 5.1

3-Aminopyrroles of formula I can be incorporated as actives in the formulation of capsules. Accordingly, the active compound is suspended in the required amount in polyethylene glycol and is incorporated into a mixture of 1 part by weight gelatin, 5 parts by weight glycerol, and 2 parts by weight water.

Alternatively the active 3-aminopyrrole can be added to a mixture of 5 parts by weight lactose, 5 parts by weight potato starch, and 1 part by weight magnesium stearate.

Other dosage forms, such as, coated pills, tablets, lozenges, granulates, powders, aqueous suspensions, syrups and the like can also be prepared.

We claim:

1. A 3-aminopyrrole of Formula (I)

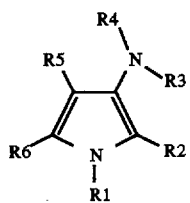

(I)

wherein $R^1$ is H, or a methyl, ethyl, or benzyl residue, $R^2$ is H, or a formyl, acetyl, methoxycabonyl, or ethoxycarbonyl residue, $R^3$ is H, or a methyl, or phenyl residue, $R^4$ is a methyl or phenyl residue, or $R^3$ and $R^4$ are taken together with the nitrogen from a morpholino, pyrrolidino or piperidino residue, $R^5$ is a phenyl, p-toluyl, p-ethylphenyl, m-anisyl, p-anisyl, 4-fluorophenyl, 4-chlorophenyl, 3-bromophenyl, 4-bromophenyl, 3,4-dimethoxyphenyl or 4-biphenyl residue, and $R^6$ is H, or $R^5$ and $R^6$ taken together are a tetramethylene residue, or a pharmaceutically acceptable salt thereof, with the proviso that if $R^1$ and $R^6$ are respectively hydrogen and $NR^3R^4$ morpholino then $R^2$ and $R^5$ respectively are not methoxycarbonyl and phenyl, ethoxycarbonyl and phenyl, methoxycarbonyl and p-chlorophenyl, methoxycarbonyl and p-toyl, ethoxycarbonyl and p-tolyl, or methoxycarbonyl and p-anisyl.

2. The following compounds according to claim 1:

methyl ester of 3-dimethylamino-4-phenylpyrrole-2-carboxylic acid;

methyl ester of 4-phenyl-3-pyrrolidinopyrrole-2-carboxylic acid;

ethyl ester of 4-phenyl-3-pyrrolidinopyrrole-2-carboxylic acid;

methyl ester of 1-methyl-3-morpholino-4-phenylpyrrole-2-carboxylic acid;

methyl ester of 1-benzyl-3-morpholino-4-phenylpyrrole-2-carboxylic acid;

methyl ester of 1-ethoxycarbonylmethyl-3-morpholino-4-phenylpyrrole-2-carboxylic acid;

methyl ester of 1-methyl-3-morpholino-4-(p-tolyl) pyrrole-2-carboxylic acid;

ethyl ester of 3-piperidino-4-(p-tolyl)pyrrole-2-carboxylic acid;

methyl ester of 3-morpholino-4-(p-tolyl)pyrrole-2-carboxylic acid;

methyl ester of 4-(m-anisyl)-3-morpholinopyrrole-2-carboxylic acid;

methyl ester of 4-(p-anisyl)-3-morpholinopyrrole-2-carboxylic acid;

ethyl ester of 4-(p-anisyl)-3-morpholinopyrrole-2-carboxylic acid;

methyl ester of 4-(p-fluorophenyl)-3-morpholinopyrrole-2-carboxylic acid;

ethyl ester of 4-(p-chlorophenyl)-3-morpholinopyrrole-2-carboxylic acid;

methyl ester of 4-(p-chlorophenyl)-1-methyl-3-morpholinopyrrole-2-carboxylic acid;

ethyl ester of 4-(p-chlorophenyl)-1-methyl-3-morpholinopyrrole-2-carboxylic acid;

nethyl ester of 1-benzyl-4-(p-chlorophenyl)-3-morpholinopyrrole-2-carboxylic acid;

methyl ester of 4-(p-chlorophenyl)-3-piperidinopyrrole-2-carboxylic acid;

methyl ester of 4-(m-bromophenyl)-3-morpholinopyrrole-2-carboxylic acid;

methyl ester of 4-(p-bromophenyl)-3-morpholinopyrrole-2-carboxylic acid;

methyl ester of 4-(p-bromophenyl)-1-methyl-3-morpholinopyrrole-2-carboxylic acid;

methyl ester of 4-(p-bromophenyl)-1-ethyl-3-morpholinopyrrole-2-carboxylic acid;

methyl ester of 3-morpholino-4-(p-phenylphenyl)pyrrole-2-carboxylic acid;

methyl ester of 4-(3,4-dimethoxyphenyl)-3-morpholinopyrrole-2-carboxylic acid;

ethyl ester of 3-anilino-4,5-pentamethylenepyrrole-2-carboxylic acid; and 2-acetyl-4-(p-chlorophenyl)-3-morpholinopyrrole.

3. A process for preparing the 3-aminopyrrole of claim 1, which comprises oxidative ring closure of an aminoacrylic derivative of formula (II)

in the presence of an oxidizing agent, during the leaving of S, wherein $R^1$, $R^2$, $R^3$, $R^4$, $R^5$, and $R^6$, have the same meanings as given above.

4. The process of claim 3, wherein said ring closure is carried out in the presence of hydrogen peroxide, or another peroxide or persulfate oxidizing agent.

5. A process for preparing a 3-aminopyrrole of claim 1, wherein $R^1$ is alkyl, cycloalkyl, or aralkyl, methyl, ethyl, or benzyl which comprises reacting (i) a 3-aminopyrrole of formula (IX) which is not substituted in the 1-position

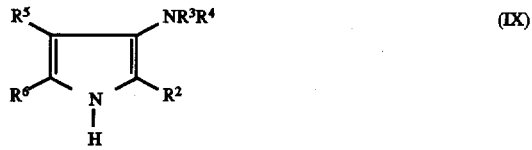

wherein $R^1$ has the same meaning has given above, and $R^2$, $R^3$, $R^4$, $R^5$, and $R^6$, have the same meaning as given in claim 1, with (ii) an alkylating agent of formula (X)

wherein $R^1$ has the same meaning as given above, and $Y^2$ is a leaving group, and with (iii) a base.

6. The process of claim 5, wherein the reaction is carried out with an alkylating agent which is an alkyl halide, aryl halide, alkyl sulfonate, dialkyl sulfate trialkyloxonium salt, or diazomethane, in the presence of a base.

7. The process of claim 5, wherein said leaving group is a halogen, sulfonyloxy or diazo residue.

* * * * *